United States Patent [19]

Wise

[11] 4,388,248

[45] * Jun. 14, 1983

[54] AMMOXIDATION PROCESSES

[75] Inventor: Kenneth V. Wise, Ballwin, Mo.

[73] Assignee: Monsanto Company, St. Louis, Mo.

[*] Notice: The portion of the term of this patent subsequent to Jul. 31, 1996, has been disclaimed.

[21] Appl. No.: 313,140

[22] Filed: Oct. 20, 1981

Related U.S. Application Data

[63] Continuation of Ser. No. 973,429, Dec. 26, 1978, abandoned, which is a continuation-in-part of Ser. No. 866,596, Jan. 3, 1978, Pat. No. 4,162,992.

[51] Int. Cl.$^3$ ............................................ C07C 120/14
[52] U.S. Cl. .................................................. 260/465.3
[58] Field of Search ...................................... 260/465.3

[56] References Cited

U.S. PATENT DOCUMENTS 3,681,421 8/1972 Barclay et al. .................... 260/465.3
3,879,435 4/1975 Gasson et al. .................... 260/465.3
4,162,992 7/1979 Wise ............................. 260/465.3 X Primary Examiner—Joseph P. Brust
Attorney, Agent, or Firm—Roger R. Jones; Richard D. Stone; A. Milton Cornwell

[57] ABSTRACT

An oxidation and ammoxidation process is disclosed which employ catalysts which have the empirical formula $Sb_aV_bTi_cO_x$, wherein a is at least 6, b is 1, and c is a number such that the ratio c/a is at least 0.5, and x is a number taken to satisfy the valence requirements of the Sb, V and Ti present in the catalyst. Such catalysts may be optionally supported on conventional supports, or may be unsupported.

10 Claims, No Drawings

AMMOXIDATION PROCESSES

PARENT APPLICATION DATA

This application is a continuation of applicant's parent application Ser. No. 973,429, filed Dec. 26, 1978, and now abandoned, which in turn is a continuation-in-part of application Ser. No. 866,596, filed Jan. 3, 1978, now U.S. Pat. No. 4,162,992, issued July 31, 1979.

BACKGROUND OF THE INVENTION

This invention relates to oxidation and/or ammoxidation catalysts containing the elements antimony, vanadium, titanium and oxygen, and to a method of preparing such catalysts. In another aspect, this invention relates to a process employing such catalysts.

It is well known that olefins can be oxidized to oxygenated hydrocarbons such as unsaturated aldehydes and acids, for example, acrolein and methacrolein, and acrylic and methacrylic acid. It is also well known that olefins can be ammoxidized to unsaturated nitriles such as acrylonitrile and methacrylonitrile. The value of such oxygenated hydrocarbons and unsaturated nitriles is generally well recognized with acrylonitrile being among the most valuable monomers available to the polymer industry for producing useful polymeric products.

Various catalytic processes are known for the oxidation and/or ammoxidation of olefins. Such processes commonly react an olefin or an olefin-ammonia mixture with oxygen in the vapor phase in the presence of a catalyst. For the production of acrolein and acrylonitrile, propylene is the generally used olefin reactant and for the production of methacrolein and methacrylonitrile, isobutylene is the generally used olefin reactant.

Many catalysts are disclosed as suitable in the foregoing reactions. One such catalyst is described in Example 3 of U.S. Pat. No. 3,681,421. This catalyst employs oxides of antimony, vanadium, and at least one additional polyvalent metal which may be titanium in the proportion of 1 gram atom of antimony, 0.12–0.5 gram atoms of vanadium, and 0.25–0.5 gram atoms of titanium. Under the conditions of that example a yield of 56% of acrylonitrile was obtained using propylene, ammonia, air, and steam as reactants.

It is well known that the economics of acrylonitrile manufacture dictate increasingly higher yields and selectivity of conversion of the reactants to acrylonitrile in order to minimize the difficulties attending purification of the product and handling of large recycle streams. Moreover, it is known that prior art catalysts such as that described in U.S. Pat. No. 3,681,421 frequently produce relatively large quantities of undesired oxygen-containing by-products such as $CO_2$, acrolein, and/or acrylic acid which must be removed in purification of the acrylonitrile.

SUMMARY OF THE INVENTION

It is an object of this invention to provide a catalyst which gives surprisingly higher yields and selectivity of conversion of propylene, ammonia, and air to acrylonitrile than do prior art catalysts.

It is a further object to provide a catalyst which minimizes the production of oxygenated by-products of acrylonitrile, such as $CO_2$, acrolein, acrylic acid, and the like.

Still another object is to provide a catalyst which exhibits substantially its full activity immediately upon startup of an ammoxidation process, i.e., which requires no break-in period under ammoxidation conditions in order to exhibit its full efficiency in terms of activity and selectivity.

A further object of this invention is to provide a process for manufacture of such a catalyst.

In another aspect, it is an object of this invention to provide an ammoxidation process which employs such a catalyst.

To achieve these and other objects which will become apparent, a catalyst is provided having the empirical formula $Sb_aV_bTi_cO_x$, where a is at least 6, such as 6 to 36, and more preferably 12 to 27, b is 1, and c is a number such that the ratio of c/a is at least 0.5, such as 0.75 to 3.0, preferably 1.0 to 2.0, and x is a number taken to satisfy the valence requirements of the Sb, V and Ti in the oxidation states in which they exist in the catalyst.

Catalysts according to this invention are preferably prepared by forming an aqueous slurry of $Sb_2O_3$, $V_2O_5$, and $TiO_2$ containing the metal ions $Sb^{+3}$, $V^{+5}$, and $Ti^{+4}$ in the desired atomic ratios. However, other compounds of antimony, vanadium, and titanium may be used as starting materials in the preparation of suitable catalysts. Suitable sources of antimony include $Sb_2O_4$, $Sb_2O_5$ (in the form of a hydrate or as a sol), Sb metal, $SbCl_5$, and $SbCl_3$; suitable sources of vanadium include $NH_4VO_3$, $VOSO_4$, $VOC_2O_4$, $V_2O_4$, $V_2O_3$, vanadyl acetylacetonate, and vanadium acetylacetonate; and suitable sources of titanium include $TiOSO_4$, $TiCl_4$, $Ti_2O_3$, and TiO. The slurry, after initimate mixing, is then heated to remove the bulk of the aqueous phase. The concentrated slurry contains a certain amount of water and it is desirable to remove this water by some form of drying process to form a dry catalyst precursor. This can take the form of a simple oven-drying process in which the water containing solid phase is subjected to a temperature that is sufficiently high to vaporize the water and completely dry out the solid phase.

An alternate drying process which may be employed is the so-called spray-drying process in which water-containing solid phase particles are sprayed into contact with hot gas (usually air) so as to vaporize the water. The drying is controlled by the temperature of the gas and the distance the particles travel in contact with the gas. It is generally undesirable to adjust these parameters to achieve too rapid drying as this results in a tendency to form dried skins on the partially dried particles of the solid phase which are subsequently ruptured as water occluded within the particles vaporizes and attempts to escape. By the same token, it is desirable to provide the catalyst in a form having as little occluded water as possible. Therefore, where a fluidized bed reactor is to be used and microspheroidal particles are desired, it is advisable to choose the conditions of spray-drying with a view of achieving substantially complete drying without particle rupture.

Following the drying operation, the catalyst precursor is calcined to form the catalyst. The calcination process is usually conducted in air at essentially atmospheric pressure and at a temperature of above about 500° C., such as from about 500° to about 875° C., and preferably at about 750° C. The time to complete the calcination can be anything up to 10 hours, but for most purposes, the calcination need take only from about 1 to 2 hours, preferably about 2 hours at the preferred calcination temperature of about 750° C.

In some applications, it may be advantageous to include in the catalyst a support material which may or may not be active catalytically but which functions by providing a large surface area for the catalyst and by creating a harder and more durable catalyst for use in the highly abrasive environment of a fluidized bed reactor. This support material can be any of those commonly proposed for such use such as, for example, silica, zirconia, alumina and titania or other oxide substrates. From the point of view of availability, cost and performance silica is usually a satisfactory support material and is preferably in the form of silica sol for easy dispersion; however, from the point of view of catalyst selectivity, it may be advantageous to use an antimony pentoxide ($Sb_2O_5$) sol as the support for catalysts of this invention should a supported catalyst be required.

The proportions in which the components of the supported catalysts are present can vary widely but it is usually preferred that the support provides from 0 to 50% and most preferably about 5 to 35 by weight of the total combined weight of the catalyst and the support. To incorporate a support into the catalyst, the support material is preferably added to the slurry containing the Sb, V, and Ti compounds discussed above.

The catalyst preparation of the invention yields a catalyst that is particularly useful in the production of acrylonitrile from propylene and in that which follows specific reference is made to that process although it should be understood that the described catalyst is also useful for ammoxidation of other olefins and for oxidation of aliphatic olefins to aldehydes and acids.

In the most frequently used ammoxidation processes, a mixture of olefin, ammonia and oxygen (or air) is fed into a reactor and through a bed of catalyst particles. The reaction temperature is usually in the range of 400° C. to 550° C. and preferably 450° C. to 525° C., and the pressure is 1 to 6 atmospheres (1.03 to 6.20 $kg/cm^2$) absolute. The ammonia and olefin are required stoichiometrically in equimolar amounts, but it is usually necessary to operate with a molar ratio of ammonia to olefin in excess of 1 to reduce the incidence of side reactions. Likewise, the stoichiometric oxygen requirement is 1.5 times the molar amount of olefin but, desirably an oxygen to propylene ratio of 1.6 to 2.4, and preferably 1.9 to 2.0, is employed. The feed mixture is commonly introduced into the catalyst bed at a W/F (defined as the weight of the catalyst in grams divided by the flow of reactant stream in ml/sec. at standard temperature and pressure) in the range of about 3.5 to about 15, preferably from about 5 to about 10.

The ammoxidation reaction is exothermic, and for convenience in heat distribution and removal the catalyst bed is desirably fluidized; however, fixed catalyst beds may be employed with alternative heat removal means such as cooling coils within the bed.

The catalyst prepared by the process of the present invention is particularly well adapted for use in such a process and in what follows its effectiveness and advantages over prior art catalysts are demonstrated in the context of that process.

SPECIFIC EMBODIMENTS

As has been stated above, the catalyst of the invention has the empirical formula, $Sb_aV_bTi_cO_x$, where a is at least 6, b is 1, and c is a number such that the ratio c/a is at least 0.5, and x is a number taken to satisfy the valence requirements of the Sb, V, and Ti present in the catalyst, optionally dispersed on a finely divided support which represents from 0 to 50% of the supported catalyst weight. In the examples that are presented below, specific compositions within this range were prepared and employed as catalysts in the ammoxidation of propylene to produce acrylonitrile.

EXAMPLE 1

A catalyst having the composition $Sb_{12}V_1Ti_{18}O_x$ was prepared by the following method. 34.98 grams of $Sb_2O_3$, 1.82 grams of $V_2O_5$, and 28.77 grams of $TiO_2$ were placed in a beaker and slurried with about 50 milliliters of distilled water. The slurry was stirred well to insure intimate mixing of the suspended solid components and then was heated on a hot plate to remove the bulk of the water. The resulting wet mixture of antimony, vanadium, and titanium oxides was dried in air overnight at 130° C. and then calcined at 750° C. for two hours in air.

The catalyst so prepared was placed in a fluidized bed reaction vessel having an inside diameter of about 1.46 centimeters. A reactant mixture of 17.50 volume % $O_2$, 8.60 volume % propylene ($C_3H_6$), 8.90 volume % $NH_3$, and the balance helium was passed upward through the catalyst at a rate of 0.133 milliliters per second (measured at standard temperature and pressure) of reactant gas per second per gram of catalyst, giving a value of W/F (as described below) of 7.5. The reactor vessel was maintained at a temperature of 485° C. and a pressure of 2.09 $kg/cm^2$ absolute during this run. The reactor effluent gas was analyzed after two hours of operation and the results were as follows:

TABLE 1

| Component | Volume Percent |
| --- | --- |
| $O_2$ | 1.15 |
| $N_2$ | .03 |
| CO | .74 |
| $CO_2$ | 2.49 |
| $NH_3$ | .85 |
| Propylene ($C_3H_6$) | .34 |
| HCN | 1.65 |
| $H_2O$ | 24.54 |
| Acrolein (ACR) | .16 |
| Acetonitrile (AcN) | .10 |
| Acrylonitrile (AN) | 5.86 |

Based on these analytical results, an acrylonitrile yield of 71.7% and a selectivity to acrylonitrile of 74.8% were achieved at a propylene conversion of 95.9%. As used herein, these terms are defined as follows:

1. W/F is defined as the weight of the catalyst in grams divided by the flow rate of reactant stream in ml/sec. measured at S.T.P.

2. Propylene ($C_3H_6$) conversion is defined as:

$$\frac{\text{Mols } C_3H_6 \text{ in feed} - \text{mols } C_3H_6 \text{ in effluent}}{\text{Mols } C_3H_6 \text{ in feed}} \times 100$$

3. Acrylonitrile (AN) selectivity is defined as:

$$\frac{\text{Mols AN in effluent}}{\text{Mols } C_3H_6 \text{ converted}} \times 100$$

4. Acrylonitrile (AN) yield is defined as:

$$\frac{\text{Mols AN formed}}{\text{Mols } C_3H_6 \text{ in feed}} \times 100$$

EXAMPLES 2-11

Unsupported catalysts were prepared using as starting materials $Sb_2O_3$, $V_2O_5$, and $TiO_2$ and following the preparation procedure (including oven drying at 130° C. and calcination at 750° C. for 2 hours) of Example 1, but varying the amounts of the starting materials to obtain catalysts having various ratios of catalytic metal components according to this invention.

These catalysts were each loaded into the fluidized bed reactor used in Example 1, and the feed stream of Example 1 was introduced into the reactor at a W/F of 7.5. The results are shown in the following Table 2:

TABLE 2

| Example | Catalyst $Sb_aV_bTi_cO_x$ | a | c/a | Reaction Temp. (°C.) | % AN Yld. | % AN Selc. | % $C_3H_6$ Conv. |
|---|---|---|---|---|---|---|---|
| 2 | $Sb_{12}V_1Ti_{12}$ | 12 | 1.0 | 492 | 70 | 74 | 94 |
| 3 | $Sb_{12}V_1Ti_{15}$ | 12 | 1.25 | 485 | 71 | 74 | 96 |
| 4 | $Sb_{18}V_1Ti_{18}$ | 18 | 1.0 | 480 | 70 | 75 | 94 |
| 5 | $Sb_{36}V_1Ti_{36}$ | 36 | 1.0 | 486 | 68 | 75 | 91 |
| 6 | $Sb_{27}V_1Ti_{27}$ | 27 | 1.0 | 485 | 71 | 76 | 94 |
| 7 | $Sb_{12}V_1Ti_{24}$ | 12 | 2.0 | 485 | 70 | 75 | 93 |
| 8 | $Sb_{36}V_1Ti_{54}$ | 36 | 1.5 | 480 | 67 | 75 | 89 |
| 9 | $Sb_6V_1Ti_9$ | 6 | 1.5 | 467 | 69 | 73 | 95 |
| 10 | $Sb_9V_1Ti_9$ | 9 | 1.0 | 480 | 68 | 75 | 91 |
| 11* | $Sb_8V_1Ti_{48}$ | 8 | 6.0 | 434 | 60 | 67 | 89 |

*In Examples 2-10 the reaction was conducted at an absolute pressure of 2.09 kg/cm² absolute, while in Example 11 the pressure was 1.18 kg/cm² absolute.

EXAMPLES 12-21

To demonstrate the use of materials other than the preferred $Sb_2O_3$, $V_2O_5$ and $TiO_2$ to prepare catalysts according to this invention, catalysts were prepared using the starting materials shown in Table 3 below. In all cases, an aqueous slurry of the starting materials was formed as in Example 1 to give Sb:V:Ti in atomic ratios of 12:1:18, although, of course, the weights of the various starting materials employed were varied from the weights of Example 1 in accordance with their molecular weights. The resulting slurries were oven dried at about 130° C. and calcined at 750° C. for 2 hours as in Example 1. Also shown in the following Table are the performance results of evaluations of these catalysts in the reactor of Example 1 at a reaction temperature of 480° C. and pressure of 2.09 kg/cm² absolute and using the feed stream composition of Example 1.

TABLE 3

| Example | Starting Materials | | | Reactor Feed W/F | % AN Yield | % AN Selectivity | % $C_3H_6$ Conversion |
|---|---|---|---|---|---|---|---|
| 12 | $Sb_2O_3$ | $NH_4VO_3$ | $TiO_2$ | 5.0 | 62 | 74 | 84 |
| 13 | $Sb_2O_3$ | $VOC_2O_4$ | $TiO_2$ | 5.0 | 63 | 71 | 89 |
| 14 | $Sb_2O_3$ | $VOSO_4$ | $TiO_2$ | 7.5 | 64 | 71 | 91 |
| 15 | $Sb_2O_3$ | Vanadyl acetylacetonate | $TiO_2$ | 7.5 | 68 | 70 | 97 |
| 16 | $Sb_2O_3$ (senarmontite crystalline structure) | $V_2O_3$ | $TiO_2$ | 7.5 | 64 | 72 | 89 |
| 17 | $Sb_2O_3$ (predominately amorphous structure) | $V_2O_5$ | $TiO_2$ | 5.0 | 70 | 72 | 96 |
| 18 | $Sb_2O_4$ | $V_2O_3$ | $TiO_2$ | 7.5 | 67 | 71 | 95 |
| 19 | $Sb_2O_3$ | $V_2O_4$ | $TiO_2$ | 7.5 | 67 | 73 | 91 |
| 20 | $Sb_2O_5$ | $V_2O_3$ | $TiO_2$ | 5.0 | 55 | 76 | 72 |
| 21 | 4 $H_2O$ $SbCl_3$ | $V_2O_3$ | $TiO_2$ | 7.5 | 64 | 70 | 91 |

EXAMPLES 22-26

To illustrate the use of materials which may be employed as supports for a catalyst according to this invention, the following catalysts were prepared. Note that in Examples 22-25, in which an $Sb_2O_5$ sol is employed, the sol serves a dual purpose; it provides all or part of the catalytic element antimony in the catalyst of this invention, and, additionally, serves as a "support" in the sense that the catalyst so produced is harder than those of the preceding Examples.

The catalysts of these Examples again had the catalytic element ratios of Sb:V:Ti of 12:1:18 as in Example 1. The catalysts of Examples 22-24 were prepared by forming an aqueous slurry containing the vanadium and titanium compounds, adding to this slurry an antimony pentoxide sol, and drying and calcining as in Example 1. The catalyst of Example 25 was likewise prepared by this procedure, except that 80% of the required antimony was supplied as $Sb_2O_3$ included in the initial slurry, and 20% of the required antimony was supplied by $Sb_2O_5$ sol added to the slurry after mixing. In Example 26, $Sb_{12}V_1Ti_{18}O_x$ prepared as in Example 1 was reslurried with $SiO_2$ sol sufficient to give 30% $SiO_2$ in the finished catalyst and recalcined at 550° C.

The catalysts of these Examples were evaluated in the reactor employed in Example 1, using the feed gas composition of that Example, W/F of 7.5, a pressure of 2.09 kg/cm² absolute and a reaction temperature of 480° C. except Example 26 where the temperature was 485° C. The results are summarized in the following Table 4:

TABLE 4

| Example | Starting Materials | % AN Yield | % AN Selec. | % $C_3H_6$ Conv. |
|---|---|---|---|---|
| 22 | $Sb_2O_5$ sol, $V_2O_3$, $TiO_2$ | 58 | 74 | 79 |
| 23 | $Sb_2O_5$ sol, $V_2O_5$, $TiO_2$ | 60 | 72 | 84 |
| 24 | $Sb_2O_5$ sol, $VOC_2O_4$, $TiO_2$ | 62 | 68 | 92 |
| 25 | $Sb_2O_5$ sol (20% of Sb) $Sb_2O_3$ (80% of Sb), $V_2O_5$, $TiO_2$ | 60 | 76.5 | 78 |
| 26 | $Sb_{12}V_1Ti_{18}$, $SiO_2$ | 64 | 71 | 90 |

EXAMPLES 27-31

To show the utility of catalysts of this invention as olefin oxidation catalysts, a $Sb_{12}V_1Ti_{18}O_x$ catalyst similar to that of Example 1 was employed in the reactor of Example 1. A feed mixture of 18.6 mol percent $O_2$, 9.7 mol percent propylene, and the balance (71.7 mol percent) helium was fed to the catalyst-containing reaction zone at a temperature of 470°-475° C., a pressure of 1.03 kg/cm², and at varying rates of W/F. Upon analysis of the reactor effluent, the following results were obtained:

| | Example: | | | | |
|---|---|---|---|---|---|
| | 27 | 28 | 29 | 30 | 31 |
| W/F | 0.65 | 1.3 | 3.25 | 6.5 | 9.75 |
| Temp. (°C.) | 470 | 475 | 475 | 470 | 474 |
| Volume Percent | | | | | |
| $O_2$ | 11.87 | 11.06 | 8.00 | 4.60 | 3.57 |
| CO | 0.58 | 0.70 | 1.26 | 1.76 | 1.91 |
| $CO_2$ | 0.58 | 0.99 | 2.66 | 4.74 | 4.12 |
| $C_3H_6$ | 6.40 | 5.81 | 4.71 | 3.54 | 3.48 |
| Methanol | 0.32 | 0.35 | 0.33 | 0.25 | 0.19 |
| Acetaldehyde | 0.45 | 0.51 | 0.49 | 0.41 | 0.33 |
| Ethanol | 0.07 | 0.03 | 0.01 | — | — |
| Acrolein | 1.05 | 1.42 | 2.17 | 2.60 | 2.48 |
| Acrolein Yield (%) | 10.8 | 14.6 | 22.4 | 26.8 | 25.6 |
| Acrolein Selec. (%) | 31.8 | 36.5 | 43.5 | 42.2 | 39.9 |

As used in these Examples, the terms acrolein yield and acrolein selectivity are defined in the same manner as the corresponding acrylonitrile yield and selectivity above.

EXAMPLES 32-41

The following Examples illustrate the effect of the variables W/F and reactor pressure on acrylonitrile yield and selectivity and on propylene conversion in the temperature range of 478°–487° C. using a $Sb_{12}V_1Ti_{1.8}O_x$ catalyst similar to that of Example 1. In Examples 32-41, a feed mixture of about 17.5 mol percent $O_2$, 8.8 mol percent propylene, 8.9 mol percent ammonia, and the balance helium was fed to reactors similar to those employed in Example 1 but of slightly different internal diameters. The results of these experiments are summarized as follows:

| Example | W/F | Temp. °C. | Absolute Pressure $kg/cm^2$ | AN Yield % | AN Selec. % | $C_3H_6$ Conv. % |
|---|---|---|---|---|---|---|
| 32 | 10 | 484 | 2.09 | 65 | 76 | 86 |
| 33 | 10 | 486 | 2.02 | 68 | 75 | 91 |
| 34 | 10 | 487 | 2.02 | 73 | 76 | 96 |
| 35 | 7.5 | 483 | 2.09 | 62 | 78 | 80 |
| 36 | 7.5 | 482 | 2.02 | 65 | 77 | 85 |
| 37 | 7.5 | 485 | 2.02 | 71 | 78 | 91 |
| 38 | 7.5 | 478 | 1.17 | 60 | 82 | 73 |
| 39 | 7.5 | 483 | 2.09 | 62 | 78 | 80 |
| 40 | 10 | 478 | 1.17 | 63 | 81 | 77 |
| 41 | 10 | 484 | 2.09 | 65 | 76 | 86 |

The above Examples are for the purpose of illustrating the invention only and are not considered as limiting the scope thereof in any way.

It will be obvious to those skilled in the art that it is possible to devise modifications and variations of the invention herein disclosed. Accordingly, it is intended that all such modifications and variations which reasonably fall within the scope of the appended claims be included herein.

I claim:

1. A process for the production of acrylonitrile which comprises reacting at an elevated temperature in the vapor phase propylene, ammonia, and molecular oxygen over a catalyst having catalytic components consisting essentially of compounds of antimony, vanadium, titanium and oxygen, said catalytic components having the empirical formula $$Sb_aV_bTi_cO_x$$

wherein a is at least 6, b is 1, and c is a number such that the ratio of c/a is from 0.75 to 3, and x is a number taken to satisfy the valence requirements of the metal ions present.

2. A process according to claim 1 wherein a is from 8 to 36.

3. A process according to claim 1 wherein a is from 12 to 27.

4. A process according to claim 1 wherein the ratio c/a is from 1 to 2.

5. A process according to claim 1 wherein said catalyst includes a catalyst support comprising up to about 50% of the total weight of the catalyst.

6. A process according to claim 1 wherein said process is conducted at a pressure of about 1.03 to about 6.20 $kg/cm^2$.

7. A process according to claim 1 wherein the temperature is from about 400° to about 550° C.

8. A process according to claim 7 wherein the temperature is from about 450° to about 525° C.

9. A process according to claim 1 wherein the flow rate W/F is from about 3.5 to about 15 gm·sec/ml.

10. A process according to claim 9 wherein W/F is from about 5 to about 10 gm·sec/ml.

* * * * *